(12) United States Patent
Heichberger

(10) Patent No.: US 8,637,299 B2
(45) Date of Patent: Jan. 28, 2014

(54) METHOD FOR CAPTURE CARBON AND STORAGE (CCS PROCESS) FROM COAL FUEL GAS AND THE STORAGE AS BIOFUELS: OIL, GASOLINE, BIODIESEL, JET FUEL, ETHANOL, AND METHANE

(76) Inventor: Albert Norman Heichberger, Jacksonville, FL (US)

( * ) Notice: Subject to any disclaimer, the term of this patent is extended or adjusted under 35 U.S.C. 154(b) by 0 days.

(21) Appl. No.: 13/207,853

(22) Filed: Aug. 11, 2011

(65) Prior Publication Data

US 2013/0040349 A1  Feb. 14, 2013

(51) Int. Cl.

| A62D 3/00 | (2007.01) |
| A62D 3/02 | (2007.01) |
| B09B 1/00 | (2006.01) |
| B09C 1/10 | (2006.01) |
| C11C 1/00 | (2006.01) |
| C02F 1/02 | (2006.01) |
| C02F 3/00 | (2006.01) |
| C02F 3/34 | (2006.01) |
| D06M 16/00 | (2006.01) |

(52) U.S. Cl.
USPC ........... 435/262; 210/600; 210/601; 210/603; 435/262.5; 435/264; 435/266; 435/271; 435/800; 435/801; 435/946

(58) Field of Classification Search
None
See application file for complete search history.

(56) References Cited

U.S. PATENT DOCUMENTS

| 4,253,271 | A | 3/1981 | Raymond ........................ 47/1.4 |
| 4,498,303 | A | 2/1985 | Heichberger |
| 4,572,728 | A | 2/1986 | Heichberger |
| 4,639,262 | A | 1/1987 | Heichberger |
| 4,977,745 | A | 12/1990 | Heichberger |
| 6,008,028 | A | 12/1999 | Bender et al. ................. 435/177 |
| 2008/0135474 | A1 | 6/2008 | Limcaco ....................... 210/602 |
| 2009/0227003 | A1* | 9/2009 | Blotsky et al. ............. 435/257.1 |
| 2011/0143012 | A1* | 6/2011 | Rettenmaier ................. 426/648 |

OTHER PUBLICATIONS

A Look Back at the U.S. Department of Energy's Aquatic Species Program, "Bio-diesel from Algae", Jun. 1998, National Renewable Energy Laboratory, 1617 Cole Boulevard, Golden, CO 80401-3000.

* cited by examiner

*Primary Examiner* — Debbie K Ware

(57) ABSTRACT

A Capture Carbon Storage (CCS) Process for the economical capture of carbon dioxide from coal fuel gas, and the storage of the carbon dioxide as lipid oil or the use of the environmentally begin oil for transportation. The lipid oil may be refined into gasoline, biodiesel fuel, jet fuel, ethanol, and methane which provide a renewable energy resource for the United State's future energy needs. It is a new fuel form which has been both chemically and physically altered to reduce the emissions of carbon dioxide. It is a coal cleaning/upgrading process which produces a refined fuel, Hydrogen, that may be used to produce electricity and an environmentally begin biofuel for transportation. The renewable fuel will produce no carbon foot print at the internal combustion engine's exhaust pipe. The CCS Process will produce a 100% reduction in carbon dioxide ($CO_2$) emissions into the atmosphere and thereby, stop the Global Warming.

4 Claims, 5 Drawing Sheets

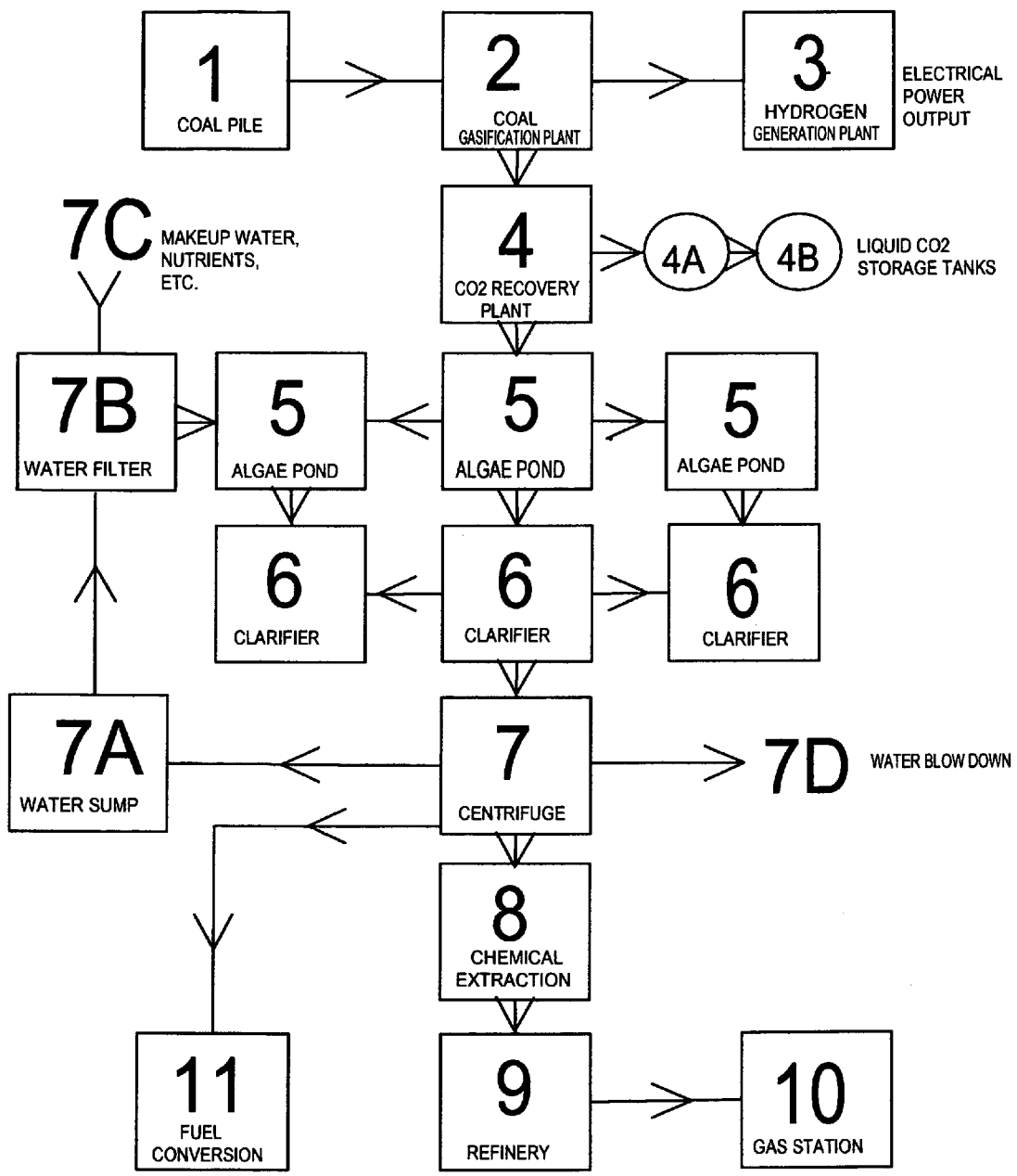
"FIG. 1"

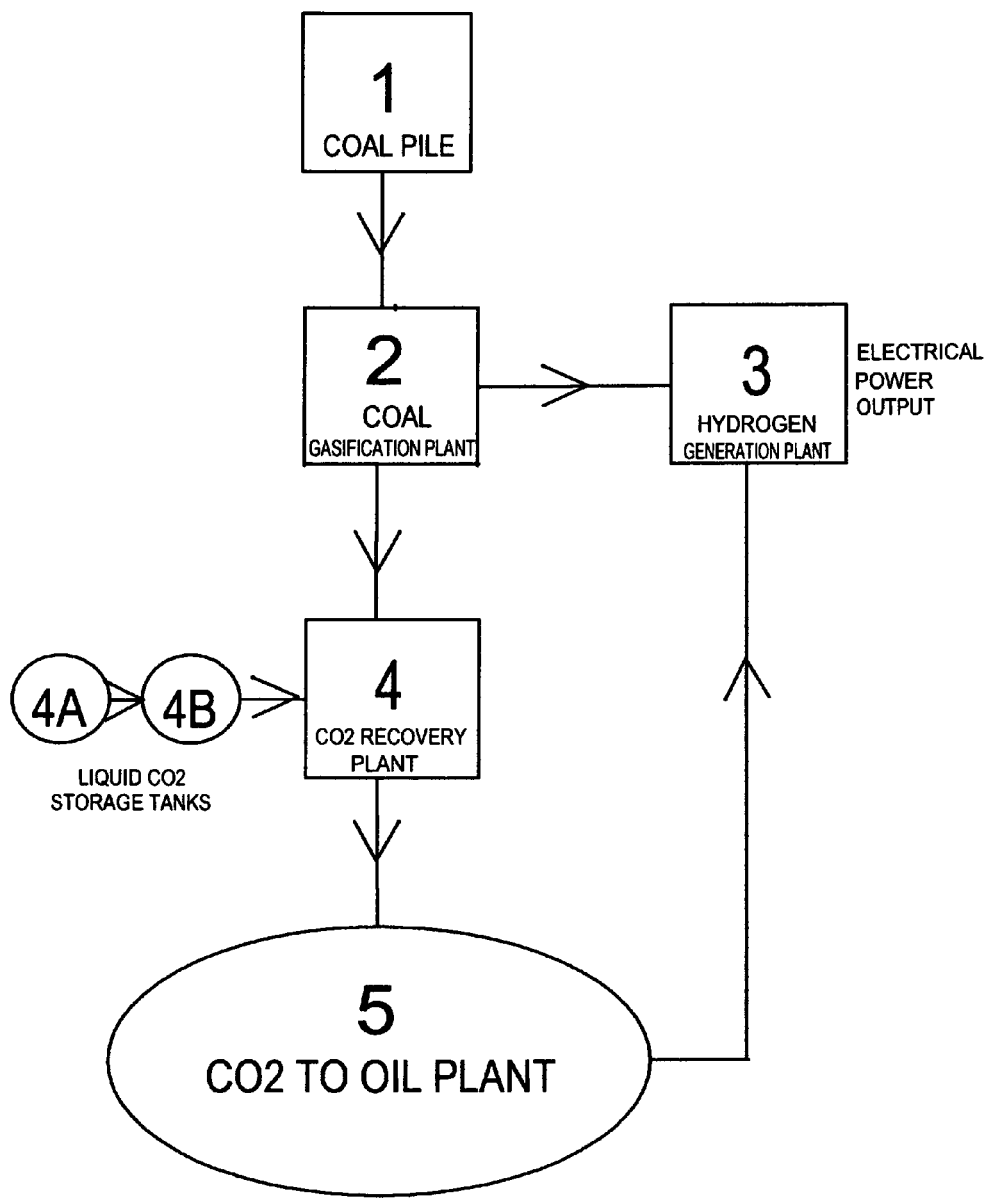
"FIG. 2"

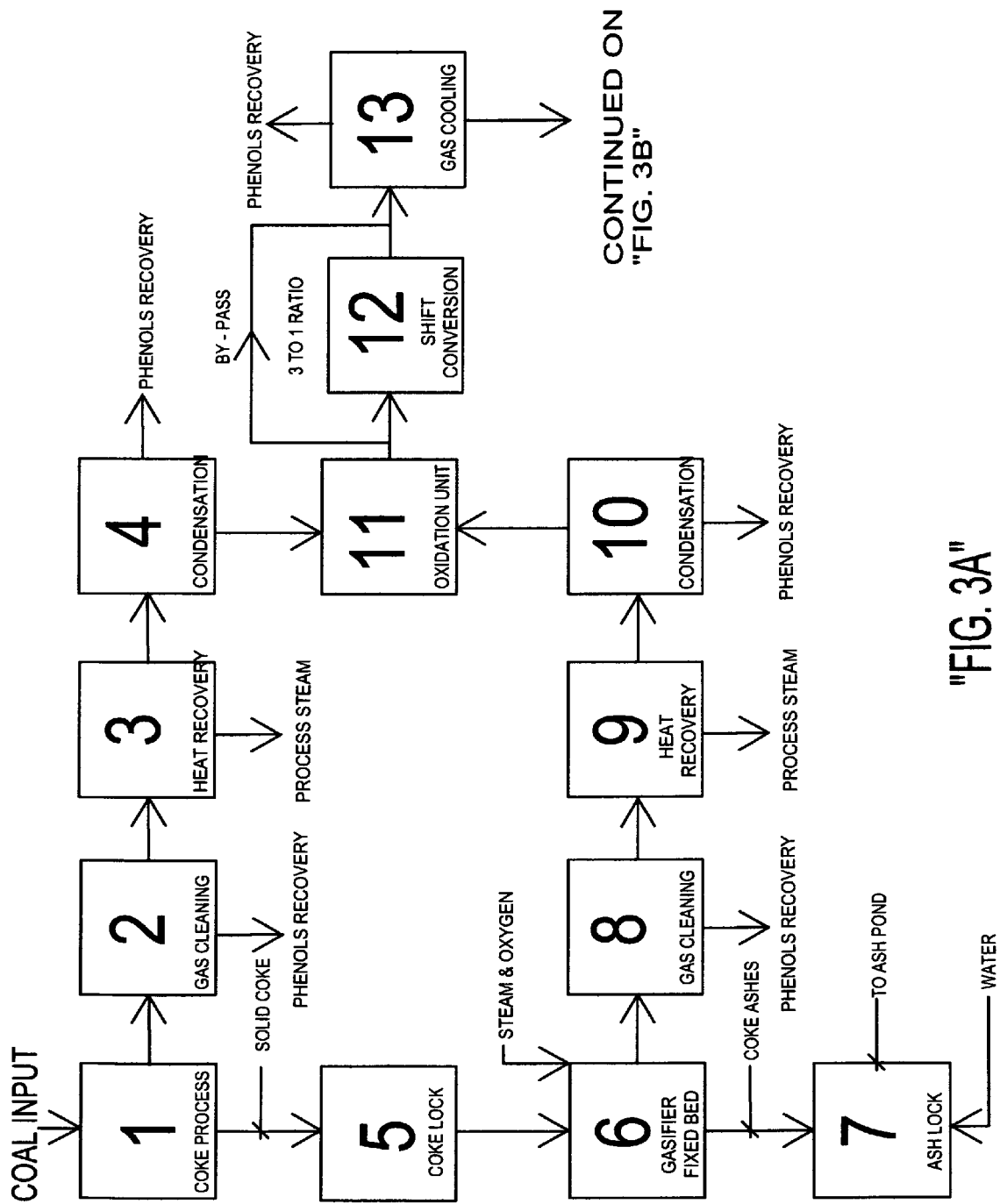
"FIG. 3A"

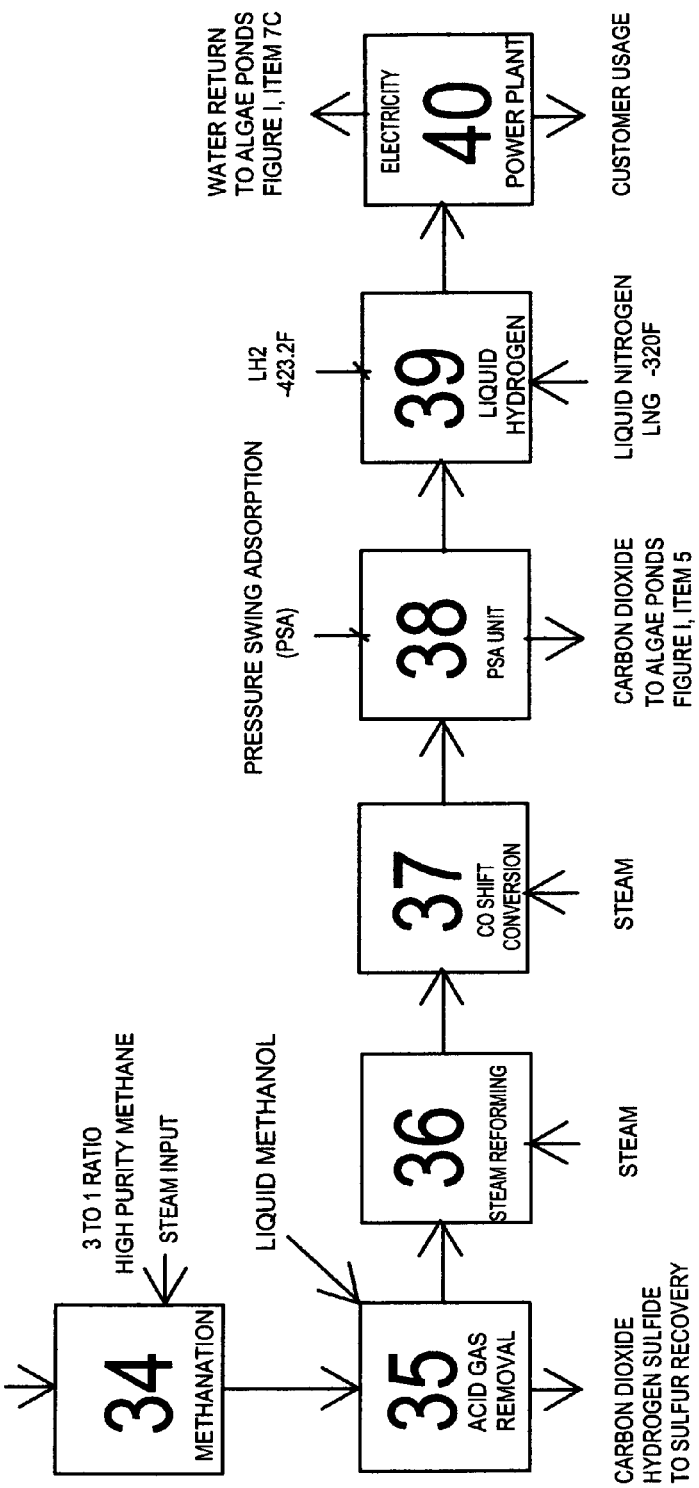
"FIG. 3B"

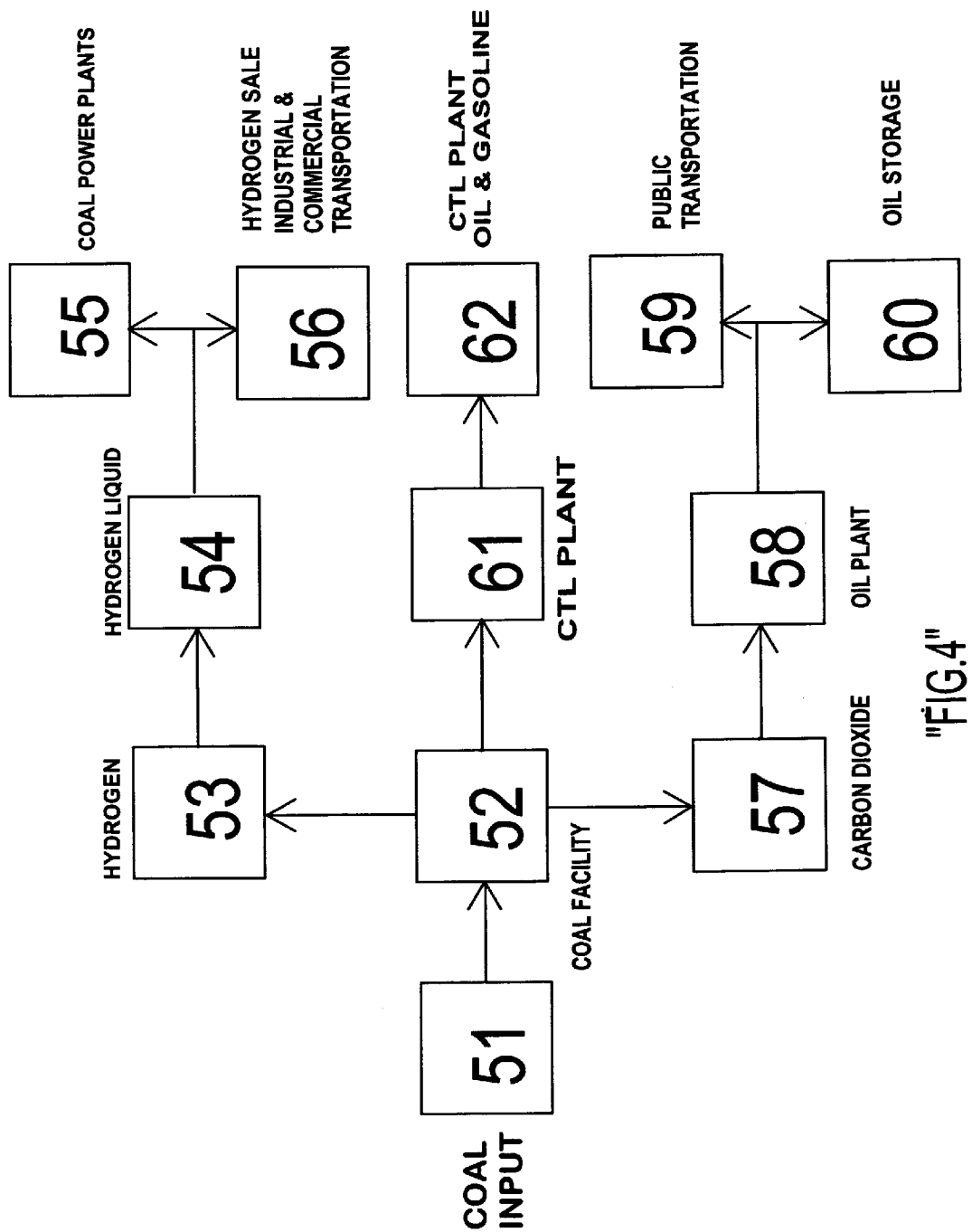
"FIG.4"

METHOD FOR CAPTURE CARBON AND STORAGE (CCS PROCESS) FROM COAL FUEL GAS AND THE STORAGE AS BIOFUELS: OIL, GASOLINE, BIODIESEL, JET FUEL, ETHANOL, AND METHANE

CROSS-REFERENCE TO RELATED APPLICATIONS

This is related to U.S. patent application Ser. No. 07/052,723 filed May 20, 1987 now abandoned; U.S. Pat. No. 4,639,262; U.S. application Ser. No. 622,217, filed Jan. 19, 1984 now abandoned; U.S. Pat. No. 4,572,728; U.S. Pat. No. 4,498,303; and U.S. Pat. No. 4,977,745; which are all incorporated herein by reference.

TECHNICAL FIELD

This invention relates generally to the recovery of low purity carbon dioxide and relates more particularly to a process and application for conversion of carbon dioxide gas into oil in conjunction with providing an economical commercially resalable grade; oil, gasoline, biodiesel fuel, jet fuel, ethanol, and/or methane. The storage of the oil is in the Government's oil surplus storage tank farms. This is a capture carbon and storage process (CCS Process).

BACKGROUND OF THE INVENTION

The two unsolvable problems of civilization are the Global Warming and the high price of oil. This process deals and reduces both of these problems. We used one process to solve or control the other process. The Global Warming pollutant, carbon dioxide, is converted into oil. It is the same process nature uses to create oil, but instead of taking thousands of year to produce a barrel of oil, this process produces a barrel of oil in one day. This oil may be refined in a conventional petroleum refinery into; gasoline, biodiesel fuel, jet fuel, and/or ethanol. The process will produce oil for approximately US$15.00 per barrel, gasoline for US$1.50 a gallon and Biodiesel for US$1.25 a gallon. A profit of 10¢ per gallon equals $35 billion profits annually. It pays to recover the pollutant carbon dioxide. The carbon dioxide is more valuable than the produced electricity.

The process takes the element carbon and converts it to oil. Instead of taking thousands of years to do this, the process does it in one day. The oil is a renewable energy resource, with unlimited production capacity. The process produces more energy than it consumes to manufacture. It is a co-product plant; it produces oil and electricity. We elected to use coal as our feed stocks for the carbon, because of its low cost, the large reserves of coal, and because it, carbon dioxide (the carbon source), is a pollutant.

It is much easier to store the liquid oil than the gaseous or liquid carbon dioxide. The current art of storing the gaseous carbon dioxide in the earth's ground is good, but there is much more carbon dioxide to store than the average person understands. Once the oil is produced it condenses the gaseous carbon dioxide by approximately 30 to 1 ratio. In other words we have less carbon dioxide to store as a liquid. The oil may be stored in multiple tank farms, underground caves, caverns, salt mines, man-made reservoirs, and artificial lakes.

A by-product of our technology is electrical power. Our power plants are different than the current industries. Our purification is done prior to combustion. We have no coal purification train; precipitators, selective catalytic reduction (SCRs) units, sulfur scrubbers, or re-heaters. We even recover the stack gas water for use in our process. The smokestack may become obsolete. This reduces a 600 Mega Watts's electrical (MWe) power plant's construction cost by approximately US$500,000,000.00 (five hundred million dollars). The oil profits from sales increase the business' bottom line. It was our primary design goal to use all by-products of the facility.

Flue gas is converted into fuel oil, gasoline, biodiesel fuel, jet fuel, methane and/or ethanol. This project will provide a renewable domestic energy source for the United States future energy needs by an environmentally acceptable use of a coal-based fuel. It is a new fuel form, which has been both chemically and physically altered to reduce the emissions of sulfur dioxide ($SO_2$), oxides of sulfur (SOxs), and the oxides of nitrogen (NOxs). The technology will work both on a low rank and a high rank coal. It is a coal cleaning/upgrading process which produces a refined fuel that may be used either to produce electricity or an environmentally benign fuel for transportation. This technology will increase the existing power plants thermal efficiency (coal pile to bus bar) by up to 100%. The process will extend our coal reserves out to 300 to 400 years. And lastly, it will produce approximately a 100% reduction in carbon dioxide emissions.

"COKING & GASIFICATION"—The indirect benefit of the Capture Carbon and Storage (CCS) Process is the renewable production of environmentally benign fuels. The fuels can be placed into storage or used as an environmentally benign fuel. The technology produces six types of fuel as follows:
 1.) Biofuels
 2.) SNG—Methane
 3.) Syngas—Hydrogen plus Carbon monoxide
 4.) Hydrogen
 5.) Electricity
 6.) SNG for the internal combustion engine The renewable Biofuels consists of the following:
 1.) Gasoline
 2.) Biodiesel
 3.) Jet Fuel
 4.) Ethanol The SNG fuel can be used as a substitute for natural gas in existing pipelines. The Hydrogen is a benign fuel, which may be used in the transportation industry for airplanes, trains, industrial trucks and automobile transportation. The electricity is a fuel for electric motor cars, which the source fuel will not be from a polluting coal, fired power plant. It is not a coal fired electric motor. The electric motor is 95% efficient while the internal combustion engine is only 45% efficient.

The retail price for fuel products will be reduced for the public sector. The CCS Process will revolutionize the Petro-Chemical Industry, and the United States will become the biggest producer of oil in the world. The oil produced by the CCS Process is more profitable then the electricity produced in the power plant.

It is apparent that the vast coal reserves in the United States must be utilized. The CCS Process can convert these large coal reserves into oil and high BTU, 970, sulfurs free Substitute (synthetic) Natural Gas, SNG. To convert coal into environmentally benign fuel hydrogen, it requires a complete rework of the basic coal structure as we know it. Both the gasification process and the hydrogen process are commercially proven technology. Gasification is the chemical process used to change solid coal into a gas and remove the undesirable elements; sulfur, carbon dioxide, coal—tars, and phenols, etc. Gasification is not a complete combustion process (100%), because the carbon and hydrogen must be saved. There are three types of fuels; carbon, hydrogen, and sulfur.

Gasification smolders the coal just below the combustion point of the carbon in an inert atmosphere of water vapor, steam. This is an endothermic reaction, which means the coal is absorbing heat. If it was complete combustion of the coal, it would be an exothermic reaction, and the coal would produce heat. To maintain the coal at gasification temperature, a small amount of oxygen from a cryogenic air separation plant is added to the steam, which causes partial combustion of the coal, and carbon monoxide (CO) is produced. Carbon monoxide is produced from the incomplete combustion of carbon while carbon dioxide ($CO_2$) is the complete combustion of carbon.

Incomplete Combustion $2C+O_2=2CO+4,347$ BTUs per LB. of carbon

Complete Combustion $C+O_2=CO_2+14,093$ BTUs per LB. of carbon

The Carburated Water Gas produces a typical fuel gas analysis from coal gasification as follows:

| | | |
|---|---|---|
| $H_2$ | Hydrogen | 34.0% V |
| $CH_4$ | Methane | 15.5% V |
| $C_2H_4$ | Ethylene | 4.7% V |
| CO | Carbon Monoxide | 32.0% V |
| $CO_2$ | Carbon Dioxide | 4.3% V |
| $N_2$ | Nitrogen | 6.5% V |
| $O_2$ | Oxygen | 0.7% V |
| $C_6H_6$ | Benzene | 2.3% V |
| Total: | | 100.0% V |

The Nitrogen ($N_2$) is an inert gas and is carried through the gasification process. The Oxygen ($O_2$) part of the air is an oxidizer and the presence of oxygen in the flue gas signifies incomplete combustion. All the remaining gases are fuels either hydrogen or hydrocarbons.

It is our goal to produce carbon dioxide for oil production, and hydrogen for a benign fuel for combustion in a power plant's boilers to produce electricity. The oil has more monetary value than the electricity. This process is relatively simple to accomplish.

The hydrogen gas conditioning train consists of the following stages:
1. gas quench
2. water-gas shift
3. gas cooling
4; acid gas removal
5. Methanation
6. steam reforming methane
7. Carbon monoxide removal Gasification is proven commercial technology to produce methane, natural gas, from coal. This process is used for the generation of biogenous substitute natural gas (SNG), which can be feed into the existing pipe grid. The CCS Process converts methane into hydrogen using commercially proven hydrogen gas technology plus steam reforming methane to convert the methane to hydrogen. The gas industry is currently successfully converting 18,000 tons of coal per day into SNG at one production facility. The CCS Process will convert approximately 17,000 tons per day of coal into hydrogen gas and lipid oil.

When we talk of the production of biogenous natural gas substitute SNG gas, we discuss the 3 to 1 ratio, but what we are actually saying is that to produce substitute natural gas (SNG), in the total crude gas stream, 3 volumes of Hydrogen ($H_2$) to 1 volume of carbon monoxide (CO) is require.

To produce SNG—Methane (CH4) in the Methanation Unit the chemical formula is CO+3H2>CH4+H2O. This formula says it takes 3 volumes of H2+1 Volume of CO to produce 1 volume of CH4, a 3 to 1 ratio.

Therefore, we by-pass the Shift Conversion unit with approximately 50% of the crude gas stream which means we have extra CO to convert to SNG (CH4) in the Methanation Unit, for a 3 to 1 ratio.

The 32.0% V of carbon monoxide is shifted to carbon dioxide and hydrogen in a shift converter, a catalytic process whereby carbon monoxide and steam are converted to carbon dioxide and hydrogen by the overall chemical reaction as follows.

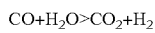

$CO+H_2O>CO_2+H_2$

The $H_2$ to $CO_2$ ratio in the crude gas must be raised to at least 3 to 1 by Volume.

$CO+3H_2>CH_4+H_2O$

Then the acid gas (carbon dioxide) is removed by a physical separation process using a liquid menthol solution.
1. In the first step, Hydrogen sulfide ($H_2S$) and carbonyl sulfide (COS) are absorbed. This provides a sulfur free (less than 0.2 ppm) Methanation feed gas.
2. In the second step, the Methanation gas is upgraded to SNG quality by the simultaneous absorption of $CO_2$ and water.

Now all the hydrocarbons must be converted to a high grade of methane plus water. Methanation is used to accomplish this conversion. The hydrocarbons are passed over a catalyst bed of nickel, which rearranges all the hydrogen molecules and carbon molecules to form a high-grade methane gas ($CH_4$). The conversion of the high-grade methane to hydrogen is directly produced by steam reforming of the methane gas.

The gasification of coal is the process of the removal of the carbon dioxide, and the manipulation of the hydrocarbons thereby, producing a high quality benign hydrogen fuel by steam reforming of the methane. Therefore, hydrogen fuel is clean coal!

The main objective of the gasification process is to produce Hydrogen ($H_2$) gas to burn in the boiler of a coal fired power plant and the capture of carbon dioxide to convert to biofuels. Hydrogen is an environmentally benign fuel and produces water vapor upon combustion. Prior technology on this scale facility is very limited. These larger facilities produced SNG and Syngas, which is hydrogen plus carbon monoxide. Carbon monoxide (CO) is a low-grade fuel and when produces carbon dioxide plus heat burned. The carbon monoxide is shifted to carbon dioxide and removed by a Pressure Swing Absorption (PSA) unit. The CCS Process emits no carbon dioxide into the atmosphere.

To convert coal into an environmentally benign fuel, hydrogen, requires a complete rework of basic coal as we know it. Pressure gasification is a thermo-chemical process used to change solid coal into a gas and remove the undesirable elements; sulfur, carbon dioxide, carbon monoxide, coal tars, and etc. The simple act of combustion gasified the solid coal into its final products of combustion—carbon dioxide, water vapor, and sulfur dioxide. Gasification is not a combustion process, because the carbon and hydrogen must be saved. It is a partial oxidation (combustion) process, which provides the heat, 2,200° F., for the thermo-chemical reaction. There are three types of fuel; carbon, hydrogen, and sulfur. Gasification simmers the coal just below the combustion point of the carbon in an inert atmosphere of water vapor, high-pressure steam. This is an endothermic reaction, which means the coal is absorbing heat. The heat supplied from the partial oxidation reaction maintains the overall gasification heat balance. If it was the combustion of coal, it would be an exothermic reaction, and the fuel would produce heat. To maintain the coal at gasification temperature, a small amount of oxygen is added to the steam, which causes incomplete combustion of the coal, carbon monoxide (CO) is produced. Carbon monoxide is an incomplete combustion of carbon while carbon dioxide ($CO_2$) is complete combustion of carbon. Typically a gasifier requires 0.3 kg $O_2$ to 0.5 kg $O_2$ per kg of dry ash free coal.

Incomplete Combustion $2C+O_2=2CO+4,347$ BTUs per LB. of carbon

Complete Combustion $C+O_2=CO_2+14,093$ BTUs per LB. of carbon

1. COKING:—The combustion of coal to produce coke is actually a heating type, oven, combustion. The coal is indirectly heated in the absence of air, which produces coke, 100% carbon (C), plus Hydrogen (H2) Gas.
2. WATER GAS:—This is what we call a Gasification Process. The gas produced by passing steam through a hot bed of coal is known as water gas. The coal combines with the steam to form hydrogen (H2) and carbon monoxide (CO). This is not a combustion process, but a partial oxidation process. Heat is added to the coal by adding a controlled amount of oxygen (O2) to elevate the coal's temperature to allow the chemical reaction to occur. It is an endothermic reaction, or the coal bed absorbs the heat.
3. PRODUCER GAS:—When coal is burned with a deficiency of air and a controlled amount of moisture (steam), producer gas is obtained. This is a controlled combustion process known as a carbon monoxide (CO) generator. It is an incomplete combustion process, which is shown by the production of carbon monoxide (CO) gas. It has a low heating value, because of the high nitrogen content from the controlled combustion process' air.

Gasification can be a one (1) stage process or a two (2) stage process. The patent application explanation will be for a two (2) stage gasification process, which contains the $1^{st}$ stage of the coke process and a $2^{nd}$ stage of carbureted water gas. The process produces 57.4% Volume hydrogen from the coking process, $1^{st}$ stage, and 34.0% Volume hydrogen by the carbureted water gas, $2^{nd}$ stage. A (1) stage gasification process can be used for carbon dioxide recovery and hydrogen production. Any of the present gasification processes may be used. A coke process is not used. They are as follows: water gas, carbureted water gas, producer gas, blast furnace gas (lean or rich), coke oven gas, or Lurgi Gas or all other gasification gases. A single stage process will produce only 2.4% Volume to 34.0% Volume of hydrogen depending on the gasification process used.

The Carbureted Water Gas Process produces a typical fuel gas analysis from coal gasification as follows:

| | | |
|---|---|---|
| $H_2$ | Hydrogen | 34.0% V |
| $CH_4$ | Methane | 15.5% V |
| $C_2H_4$ | Ethylene | 4.7% V |
| CO | Carbon Monoxide | 32.0% V |
| $CO_2$ | Carbon Dioxide | 4.3% V |
| $N_2$ | Nitrogen | 6.5% V |
| $O_2$ | Oxygen | 0.7% V |
| $C_6H_6$ | Benzene | 2.3% V |
| Total: | | 100.0% V |

The Nitrogen ($N_2$) is a byproduct of air combustion. It is an inert gas and is carried through the gasification process. The Oxygen ($O_2$) part of the air is an oxidizer and the presence of oxygen in the flue gas signifies incomplete combustion. All the remaining gases are fuels either hydrogen or hydrocarbons.

It is our goal to produce carbon dioxide for oil production, and hydrogen for a benign fuel for combustion in the power plant's boilers to produce electricity. This is relatively simple to accomplish. The hydrogen gas conditioning train consists of the following stages:

1. gas quench
2. water-gas shift
3. gas cooling
4. acid gas removal
5. Methanation
6. steam reforming methane
7. carbon monoxide removal Gasification is proven commercial technology to produce methane, substitute natural gas (SNG), from coal. This process is used for the generation of biogenous substitute natural gas (SNG), which can be feed into the existing pipe grid. The CCS Process converts methane into hydrogen using proven gas technology plus steam reforming methane to convert the methane to hydrogen. The gas industry is currently successfully converting 18,000 tons of coal per day into SNG at one production facility. The CCS Process will convert 17,000 tons per day of coal into hydrogen gas and lipid oil. The 32.0% V of carbon monoxide is oxidized to carbon dioxide in a catalytic converter. Then the 36.3% V of carbon dioxide (acid gas) is removed by a physical separation process using a liquid methanol solution. Now all the hydrocarbons must be converted to a high grade of methane. Methanation is used to accomplish this conversion. Methanation is a physical chemical process to generate methane, substitute natural gas, from a mixture of various hydrocarbon gases. The hydrocarbon is passed over a catalyst bed (nickel type), which rearranges all the hydrogen molecules and carbon molecules to form a high grade methane gas ($CH_4$).

When we talk of the production of a biogenous natural gas substitute (SNG gas), we discuss the 3 to 1 ratio, but what are we actually saying is to produce substitute natural gas (SNG), in the total crude gas stream, 3 volumes of Hydrogen (H2) to 1 volume of carbon monoxide (CO) is require, or the conversion to methane will not work.

To produce SNG—Methane (CH4) in the Methanation Unit the chemical formula is CO+3H2>CH4+H2O. This formula says it takes 3 volumes of H2+1 Volume of CO to produce 1 volume of CH4, a 3 to 1 ratio.

In the gas shift conversion to 100% $CO_2$, we are converting the CO to $CO_2$. Then we remove the $CO_2$ in the acid gas removal tower. Therefore we would not have any CO left for the Methanation unit and we could not make SNG—Methane ($CH_4$). We must not convert all the CO or $CO_2$. Therefore, as a correction, we do not want to remove the entire CO as $CO_2$ in the acid gas removal unit, but only approximately 50%. This is done by by-passing 50% of the crude gas stream around the Shift Conversion Unit via the by-pass.

Therefore, we by-pass the Shift Conversion unit with approximately 50% of the crude gas stream which means we have extra CO to convert to SNG ($CH_4$) in the Methanation Unit, for a 3 to 1 ratio. The conversion of the high grade methane to hydrogen and carbon monoxide, Syngas, is directly produced by steam reforming of methane.

The gasification of coal is the removal of the carbon and the manipulation of the hydrocarbons thereby, producing a benign hydrogen fuel. Therefore, hydrogen fuel is clean coal!

The oil conversion is accomplished by Biomass Technology. Mass cultures of microalgae will convert sunlight, water, and carbon dioxide into fuel by photosynthetic fixation of the carbon dioxide. Microalgae can produce raw feed stock in large volumes which is a basic prerequisite in mass fuel production Or as an alternative, we will produce ethanol to be used for transportation. Ethanol is ethyl alcohol; which is a colorless, limpid, volatile liquid used as a fuel for internal combustion engines or in alcoholic beverages. In 1988, gasoline and diesel fuels accounted for 42% of the energy consumed in the United States. This petroleum also contributed more than $40 billion dollars to the trade deficit.

Ethanol is NOT an environmentally benign fuel, because it produces carbon dioxide at the exhaust pipe, which is now a Government pollutant. However, it does not produce smog when burned. However, the ethanol produced by the CCS Process does not produce carbon dioxide at the exhaust pipe. The carbon dioxide is produced by the displacement method, captured from a coal plant. You cannot count the carbon dioxide twice, only once

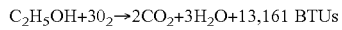
$$C_2H_5OH + 3O_2 \rightarrow 2CO_2 + 3H_2O + 13,161 \text{ BTUs}$$

All current Ethanol produced by corn and the like fermentation is a pollutant, because it produces carbon dioxide. Ethanol fuel contributes to the global warming and is a pollutant. The Ethanol produces non-pollutant carbon dioxide and water. It meets all requirements of the public law #101-549, "The 1990 Clean Air Act Amendment". In fact, it surpasses all requirements of the "Clean Air Act". Since the ethanol fuel was produced from carbon dioxide, which was vented into the atmosphere, all pollutants are eliminated—including the carbon dioxide emissions. This carbon dioxide may be stored in the Earth's atmosphere.

A coal fired power plants (with a rating of approximately 600 Mega Watts of electricity (MWe) pollution emissions can be converted into oil in an oil field producing over 14 million barrels of oil per year. Therefore, since there are approximately 1,200 coal fired generation plants (600 Mega Watts) in the United States, a potential exists of producing in excess of 16.8 billion barrels of oil a year; a total of 688 billion gallons of oil to be refined into gasoline, diesel fuel or jet fuel. More important we reduce the carbon dioxide emissions by approximately 50%.

The United States current market-place for petroleum products (approximately) is as follows: 1) Gasoline—145 billion gallons per year, 2) Diesel Fuel—100 billion gallons (est.) per year, and Jet Fuel—94 billion gallons per year for a total of 339 billion gallons of fuel. It becomes obvious that the United States needs to build more coal fired power plants. Banning coal power plants is not a solution! We need to build coal fired power plants to balance the basic equation for supply and demand; supply of 688 billion gallons per power plant and a demand of 339 billion gallons. This is the key to regulating the growth of coal fired power plant. The United States of America must use it greatest resource; coal!

COSTS:—The current Industry's cost to remove $SO_2$ by scrubbing is approximately $1.00 per million BTUs. The actual cost for CO2 reduction to the utility customer would be a credit of approximately $00.0143 per KWH, because the CCS Process costs for $SO_2$, NOxs and waste reduction are less per million BTUs when compared to current emissions technology costs.

The environmental benefits of gasification stem from the capability to achieve extremely low $SO_x$, $NO_x$, and particulate emissions from burning coal-derived gases. Sulfur in coal, for example, emerges as hydrogen sulfide and can be captured by processes presently used in the chemical industry. The capability to produce electricity, hydrogen, chemicals, or various oil combinations while eliminating nearly all air pollutants and potentially greenhouse gas emissions makes coal gasification one of the most promising technologies for energy plants of the future. The oil production eliminates all the coal gasification inefficiencies. More coal is burnt which produces more oil. The oil is worth more than the electricity. The CCS Process is a co-product plant producing electricity and oil.

This is a renewable energy resource, which will create oil plantations in the country side of the United States. The oil will be grown in oil paddies. It is a micro algae biomass process using a feed stock of carbon dioxide. Ethanol requires corn as its feed stock. This corn grows on farmland and one acre of land will produce approximately two (2) barrels of ethanol per year with one growing season. However, this same acre of farm land will produce approximately 1,450 barrels of oil per year. There is no comparison between corn Ethanol and the micro algae renewable oil. Ethanol requires more energy in its production than from corn Ethanol's energy output. The micro algae oil produces more energy than it takes to produce the oil.

CCS ethanol produces no pollutants at the exhaust pipe. It is an environmentally benign fuel. Also, gasoline produced from the algae process has no carbon foot print at the exhaust pipe, because it is made by a displacement process. The carbon dioxide was secured from the power plant's carbon dioxide emissions. Therefore, the auto has produced power with the power plant's carbon dioxide. You can't count the carbon dioxide emissions twice. There are two (2) biomass processes one with corn and the likes, and the other, algae with carbon dioxide as the feed stock, and it is obvious that the micro-algae process has a significantly higher oil yield rate and it produces no pollutants.

The oil's production facility will encompass a: 1) Fuel production facility or (coal gasification plant), 2) Carbon dioxide recovery facility, 3) Oil plantation, 4) Oil extraction facility, 3) $CO_2$ liquid storage facility (tank farm), and 4) Hydrogen fuel distribution facility (pipeline).

Background of the Algal Farm

The algae farm converts $CO_2$ recovered from the power plant flue gas into biomass, an organic form of carbon which can be stored, converted into a fuel to be burned in the internal combustion engine, or applied to cropland either as a fertilizer or as an inoculant for a self-generating nitrogen and carbon-fixing fertilizer.

In terms of fuels, the primary focus here is to convert the biomass formed from the photosynthetic fixation of $CO_2$ into oil which can be burned in the power plant, or substituted for gasoline, diesel fuel, or jet fuel. A demonstration is to anaerobically digest the biomass to form methane. Electric power can be generated during the burning of the methane, with the resultant $CO_2$ stream recycled back to the algae farm. Alternatively, the algae shells can be fermented to form ethanol with unlimited production land.

Each process requires water, $CO_2$, nutrients, and sunlight. Each produces more power than it consumes, less $CO_2$ than it consumes ($CO_2$ produced can be recycled to produce more Btus/ton $CO_2$), wastewater of the disposable effluent quality, and stabilized biomass waste streams (containing some of the carbon originally input as $CO_2$), which can be used as soil conditioner and biofertilizer. The biomass to oil conversion also consumes, and waste, some solvents. Overall the process produces more power per unit amount of $CO_2$ released to the atmosphere than the coal-fired power plant alone. The larger the algae farm is in comparison to the coal fired power plant, the less significant is this released $CO_2$. All the $CO_2$ purge and vent gas will be captured and reused to produce lipid oil.

The extent to which algal farms mitigate the release of $CO_2$ to the atmosphere depends on how efficiently input $CO_2$ is used and on how much of the waste stream $CO_2$ is recycled. In this process all the waste stream of $CO_2$ is recycled. For fuels derived from biomass which are not burned on site (e.g., those converted to gasoline, biodiesel fuel, and jet fuel) the $CO_2$ eventually finds its way to the atmosphere after a relatively short time, but more Btu's have been produced per ton of $CO_2$ released than if the $CO_2$ were never extracted from the stack gas initially. The $CO_2$ produced from burning the automotive fuel, etc. does not produce pollutant $CO_2$, because they are made from displaced $CO_2$.

Present technologies for utilizing $CO_2$ not only eventually vent the $CO_2$ to the atmosphere, but usually do not result in the production of power from each ton of vented $CO_2$ than was available from the original power plant. As the perceived danger, and hence cost of abating, the release of $CO_2$ to the atmosphere increases (Global Warming), the algae farm process becomes more and more competitive with other end uses for $CO_2$. The price of import oil keeps going up making it a highly attractive process.

The microalgae farms have the potential to be highly productive. Their operation combines the same photosynthetic principles as conventional agriculture, with the hydraulic advantages of the fermentation industry. The solar reactors proposed here are open raceway ponds, and are effective in terms of optimizing costs with process control and practicality.

The important process chemistry can be broken down into two phases: the photosynthetic carbon fixation occurring in the algae ponds and the extraction and conversion of biomass carbon into burnable fuel.

Engineering Design

"COKING" & "GASIFICATION"—A pre-combustion carbon dioxide recovery process is designed to allow the capture of the carbon dioxide at minimal cost. The coal is converted into Hydrogen to produce an environmentally benign power generation fuel. It is a two-step process. The first step is the Coke Process, and the second step is the Carbureted Water Gasification Process. The combustion of Hydrogen gas in the power generation boiler produces water vapor in the smokestack. The carbon is removed prior to combustion by coal coke process. Coke is a hard gray fuel, which is 85% carbon, coke bears the same relation to coal as does charcoal to wood. The carbon dioxide formed from the coke process is combined with the carbon monoxide, which is oxidized producing a carbon dioxide gas stream. Using a physical separation process of the Methanol type, the carbon dioxide is absorbed into the liquid Methanol solution, the first step of the process, which separates it from the other flue gases: Hydrogen, Methane, Ethylene, and Nitrogen. The process used is coking, but blast furnace gas, water gas, carbureted water gas, or producer gas is also applicable for use. When coal is indirectly heated, baked, in the absence of air or with a great deficiency of air the lighter constituents are volatilized and the heavier hydrocarbons are cracked liberating hydrogen and leave a residue of carbon. The carbonaceous residue containing the ash and a part of the hydrogen sulfide of the original coal is called "coke". An analysis of a typical Coke Oven Gas produced from bituminous coal is as follows:

| Hydrogen | $H_2$ | 57.4% by Volume |
|---|---|---|
| Methane | $CH_4$ | 28.5% by Volume |
| Ethylene | $C_2H_4$ | 2.9% by Volume |
| Carbon Monoxide | CO | 5.1% by Volume |
| Carbon Dioxide | $CO_2$ | 1.4% by Volume |
| Nitrogen | $N_2$ | 4.2% by Volume |
| Oxygen | $O_2$ | 0.5% by Volume |

A number of valuable products are recovered from these gaseous portions including ammonium sulfate, oils, and coal tars. Also, a part of the sulfur from the coal may be present as hydrogen sulfide, and carbon bisulfide gases which may be removed by scrubbing.

The second step of gasification is the production of carbureted water gas. The coke from the first step is gasified in step 2. The water gas is produced by passing steam through a hot bed of coke. The coke combines with the steam to form hydrogen and carbon monoxide. This is an endothermic reaction, and a small amount of oxygen must be admitted to the steam to maintain the coke bed at an elevated gasification temperatures. Oxygen is used so that there are no nitrogen, carbon dioxide or other combustion gases discharged to the atmosphere as purge gases. No purge gases are allowed in the CCS Process. Water Gas is enriched with oil by passing the gas through a checker-work of hot bricks sprayed with oil, which is cracked by the heat to a gas, which forms carbureted water gas.

An Analysis of a typical carbureted water gas produced from coke is as follows:

| Hydrogen | $H_2$ | 34.0% by Volume |
|---|---|---|
| Methane | $CH_4$ | 15.5% by Volume |
| Ethylene | $C_2H_4$ | 4.7% by Volume |
| Carbon Monoxide | CO | 32.0% by Volume |
| Carbon Dioxide | $CO_2$ | 4.3% by Volume |
| Nitrogen | $N_2$ | 6.5% by Volume |
| Oxygen | $O_2$ | 0.7% by Volume |
| Benzene | $C_6H_6$ | 2.3% by Volume |

The Carbon Monoxide is converted to Carbon Dioxide by oxidation ($2CO+O_2=2CO_2$). Then the carbon dioxide is removed from the gas stream by a physical separation process. Other forms of chemical absorption process may be used, such as Monoethanolamine (MEA) a chemical separation process. The carbon dioxide is removed by absorption into a solution of MEA. The Hydrogen, Methane, Ethylene, and Nitrogen are recovered from the absorption process. We reduce the steam reactivation cost to $0.0 per ton of recovered carbon dioxide by using process waste fuels; methane gas, and ethanol generated from the spent Algae shells to produce steam. The carbon dioxide recovered from the spent algae shells is converted to lipid oil, which is used to produce steam for production purposes.

The 32% v CO is converted to $CO_2$ by a shift unit in a catalytic converter. The 36.3% v Carbon Dioxide is removed from the gas stream by physical separation process using liquid methanol. The Methanation unit includes all the equipment to catalytically combine carbon monoxide and hydrogen in a 3 to 1 ratio to form methane and water. The high quality methane is then converted to hydrogen by steam reforming of the methane gas over a nickel catalyst.

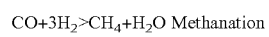
$CO+3H_2>CH_4+H_2O$ Methanation

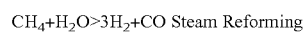
$CH_4+H_2O>3H_2+CO$ Steam Reforming

The carbon monoxide is converted to carbon dioxide by a shift conversion, which is a catalytic process whereby carbon monoxide and steam are converted or "shifted" to carbon dioxide and hydrogen by the overall chemical reaction:

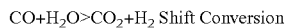
$CO + H_2O > CO_2 + H_2$ Shift Conversion

Then the carbon dioxide is removed from the gas stream by a physical separation process, which is a liquid methanol process. We reduce the methanol's pressure and temperature costs to $00.00 per ton of recovered carbon dioxide by using process waste fuels: methane gas, and ethanol generated from the spent algae shells. Further, the carbon dioxide recovered from the spent algae shells is also converted to lipid oil, which is used to produce steam for production purposes.

The main objective of the gasification process is to produce Hydrogen ($H_2$) gas to burn in the boiler of a former coal fired power plant's boiler. Hydrogen is an environmentally benign fuel and produces water vapor upon combustion. This may sound as old technology, but it is not. Prior technology on this scale facility is very limited. These larger facilities produced SNG (substitute natural gas, $CH_4$) and Syngas, which is hydrogen plus carbon monoxide. Carbon monoxide (CO) is a low grade fuel and when burned, produces carbon dioxide plus heat. The CCS Process produces no carbon dioxide into the atmosphere.

The use of a two stage gasification process in the CCS Process is unique in today's world. Most all gasification plants are, as the name implies, one stage processes. They generally are water gas, carbureted water gas, blast furnace gas or some modified form of these gases. The CCS Process uses a first stage of Coke Gas and a second stage of carbureted water gas. Coke gas is not a gasification process, because it produces carbon in the form of Coke. The CCS Process produces more hydrogen than a single stage gasification plant. The Coke Plant plus the Gasification Plant produces approximately three (3) times the amount of hydrogen gas then the Gasification Plant alone. The Coke stage produces up to 57.4% volume Hydrogen in the Coke oven gas, and produces an additional up to 34.0% volume Hydrogen in the carbureted water gas. This is a total of 91.4% volume in the two stage gasification process. The CCS Process uses the Coke (pure carbon) formed from the Coke process to gasify in the carbureted water gas process.

Hydrogen can be liquefied provided the liquefier feed is very high purity hydrogen. Liquefied hydrogen has a minimum purity of 99.995 percent. Para hydrogen liquefies at −423.2° F., and at that temperature, any contaminant in the feed stock, will be solidified and plug the liquefier.

Liquid hydrogen is produced by first precooling compressed hydrogen to liquid nitrogen temperature of −320° F., then passing it through a "guard absorber" to remove all impurities in the liquid hydrogen. It is then liquefied by further cooling the hydrogen stream to −400° F. to −410° F. This high pressure liquid stream is reduced in pressure by means of a Joules-Thompson valve and the liquid sent to storage. Refrigeration to −320° F. for liquid hydrogen plants is provided by liquid nitrogen. The approximate ratio of liquid nitrogen to hydrogen required to liquefy hydrogen is 10:1 by weight.

The hydrogen storage tanks use liquid nitrogen shielding. The ratio of gas to liquid hydrogen storage is approximately 25 to 1 cubic foot. The liquid nitrogen shield intercepts the heat leak into the liquid hydrogen. The storage tank's pressure relief valve does not vent any hydrogen and can hold liquid hydrogen for more than six months without hydrogen loss.

The CCS Process requires waste heat as follows; a.) to indirectly heat the coal during the coke process, b.) to produce steam for the Coking and Gasification process, and c.) the production of electricity. The CCS Process produces waste fuel as methane, ethanol and lipid oil. Also, the lipid oil may be used as a fuel for several process applications: a.) production of electricity, b.) reactivation of the methanol solution, and c.) for indirect heating of the coal for conversion to coke, and d.) the production of steam. The algae shells may be anaerobically digested into a biogas containing 60% methane and 40% carbon dioxide. It also can be converted into ethanol by the fermentation process. The cooker in the fermentation process produces a Biogas of 60% methane and 40% carbon dioxide. The Biogas is returned to a bulk gas separation process for removal of the methane from the carbon dioxide. The fermentation process produces 100% carbon dioxide. The carbon dioxide is used in the process to produce additional biofuels. The methane is used for heating and thereby, converting the coal to coke and for reactivation of the MEA solution. However, we can supplement the methane and ethanol with lipid oil. Another source of waste fuel is landfill gas and sewage gas. These fuels should be located locally and close to the Fuel Facility and they should be free for the taking.

The CCS Process uses gaseous and liquid Hydrogen for distribution in pipelines across the American continent. The liquid Hydrogen allows the use of a Hydrogen pipe line that is a much smaller size by volume of a Hydrogen gas pipeline. The Oxygen Generator or air reduction plant will produce liquid Nitrogen ($N_2$). The Oxygen ($O_2$) air reduction plant produces nitrogen gas as a byproduct. This nitrogen will be liquefied and used as the refrigerant to liquefy the Hydrogen gas for distribution to the various power plants by pipeline. The air is made up of approximately 80% nitrogen and 20% Oxygen so there is a large amount of liquid nitrogen available for use as a refrigerant.

"ALGAE PRODUCTION"—The CCS Process requires the capturing of the carbon dioxide from the coal fired power plant twenty-four (24) hours a day and seven (7) days a week. To accomplish this recovery rate requires 24 hour per day production of lipid oil. The conversion of carbon dioxide to oil requires water, carbon dioxide, sunlight, and nutrients. Obviously, the sunlight is not available 24 hours a day. Therefore, artificial sun light must be available. The determining factor of the sunlight is the photosynthetic efficiency of the organism itself. Photosynthetic efficiency is a measure of how much of the sun's energy available to the organism is actually captured in the organic products. The theoretical maximum efficiency is about 23%. The practical limits are usually well below this value, especially for high-intensity light, which most plants use less efficiently than they do low-intensity light. Usually, increasing light intensity beyond about 20% of full sunlight does not lead to a proportional increase in the growth rate of the cells. The ponds will be illuminated to an intensity of 5 watts per square foot and adjusted accordingly. Algal cells can use high-intensity light efficiently when exposed for short periods of time. Thus, if cells in the culture are moved from the surface to the darker areas at depth, they can sustain a higher efficiency and, hence, a higher productivity. This can be accomplished by mixing, the paddle wheel movement of the water in the Algae pond.

The other way possible would be to increase the land area by a factor of three. This would be costly. Also, the carbon dioxide would need to be stored for approximately 16 hours a day. The liquefaction and evaporation of the liquid carbon dioxide would be cost prohibitive.

"STEAM PRICE REDUCTION"—The reduction of the fuel processing costs per barrel of lipid oil of production was our first priority. Steam cost $5.00 per 1,000 lbs. of steam. It is not cheap. The use of waste fuel for the production of steam and for heating the coal in the Coke process is costly. The cost of the chemical separation is $24.00 per ton of carbon dioxide. The cost of carbon dioxide separation from the methane stream is eliminated by using the waste fuels from the anaerobic digestion of the algae spent shells. This biogas is recovered from the Digesters and contains 60% methane and 40% carbon dioxide.

The ethanol is made by the fermentation of the carbohydrates conversion to sugar. This process produces Biogas of 60% methane and 40% carbon dioxide. The methane is recovered from the cooker for waste heat for the production of steam. The ethanol produced by the fermentation is recovered for the waste heat for the production of steam or indirect heating of the coal in the Coke Process.

Another source of waste heat is from landfill gas and or sewage gas. These waste gases are free for the taking, because they are being vented to the atmosphere. Local landfill gas and sewage treatment gas will be recovered and used to produce steam.

The source for waste heat are many; steam for reactivation of the chemical solution in the reboiler's separation process; the heat required to heat the coal in the Coke Process; the high pressure steam require in the gasification process; the steam require for the hydrogen steam reforming; the steam used for the extraction of the lipid oil; and for all other steam requirements.

"WATER TEMPERATURE"—The growth of lipid oil during the evening hours will require the water to remain at a constant temperature. The evenings in the New Mexico's deserts get cold. The algae ponds must be indirectly heated to maintain the desired temperature. Indirect heaters will maintain the ponds temperature at approximately 123° F. by recirculating a slip stream of 20% pond water through a heater, which use waste process heat (methane, ethanol, lipid oil or cooling tower return water). These ponds will be heated 24 hours a day to 123° F. plus or minus ½° F. temperature. This will enhance the growth of the lipid oil.

"ALGAE FEEDING SYSTEM"—The carbon dioxide injection system will be enhanced for direct contact of the Algae and the food, carbon dioxide gas. The system will include a Contactor Tower (Absorber Tower). The tower will allow the algae and the carbon dioxide to come into contact for a time period of 6 to 8 seconds holding time. The tower also allows a greater contact surface area between the algae and the gaseous carbon dioxide. These towers are not a flooded type tower. The flow through the contactor tower will be designed for 8 seconds of holding time for a 20% slip stream of the pond's water. It will be complete with a packed bed of plastic intalox type saddles to improve the require contact time and the contact surface area between the algae and the gaseous carbon dioxide. The saddles operate as irrigated packing. The tower will be operated at a pressurized carbon dioxide atmosphere of approximately 1.0 psig. The carbon dioxide pressure will be maintained by an outlet pressure regulator. The tower will be complete with a safety valve consisting of a water seal. Additional contactor towers will be added as require to meet the desired ponds yield capacity.

The tower allows greater contact surface between the algae and the gaseous carbon dioxide. It is not a flooded tower. The saddles are irrigated.

BRIEF DESCRIPTION OF THE DRAWINGS

FIG. 1 The drawing FIG. 1 is a single line flow schematic of a disclosed embodiment of the carbon dioxide to fuel conversion facility of the present invention. It depicts the preferred mode of the embodiment of the oil, gasoline, diesel fuel, and jet fuel conversion process.

FIG. 2 The drawing FIG. 2 is a single line flow schematic view of a disclosed embodiment of the carbon dioxide to fuel conversion facility of the present invention. It depicts an advantageous mode of the embodiment of the coal fired and fuel oil fired electrical power plant fuel conversion process.

FIG. 3A The drawing FIGS. 3A is a single line flow schematics of the disclosed embodiment of the carbon dioxide to fuel conversion facility of the present invention. It depicts the preferred mode of the embodiment of FIG. 1, Item 2—"The Coal Gasification Plant."

FIG. 3B The drawing FIG. 3B is a single line flow schematics of the disclosed embodiment of the carbon dioxide to fuel conversion facility of the present invention. It is the continuation of FIG. 3A. It depicts the preferred mode of the embodiment of the Hydrogen Process.

FIG. 4 The drawing FIG. 4 is a single line flow schematic of the capture carbon and storage (CCS) facility of the present invention. It depicts the preferred mode of the embodiment all combined into the CCS Facility summary operations mode.

BRIEF SUMMARY OF THE INVENTION

This invention relates to a process for capturing of carbon dioxide from a coal fired electrical power generation plant's smoke stack and converting the $CO_2$ into oil, gasoline, biodiesel fuel, jet fuel, ethanol, and methane the process which comprises:

a. converting coal into hydrogen in a coal gasification plant;
b. converting the power plants' coal burner for hydrogen and biofuels' combustion;
c. capturing the relatively high purity $CO_2$ from the gasification plant;
d. algae in the ponds ingest the $CO_2$ and via the biomass formed from the photosynthetic fixation of $CO_2$, into an oil which can be refined into gasoline, biodiesel fuel, jet fuel, ethanol or methane;
e. each process requires water, $CO_2$, nutrients, and sun light;
f. the important process chemistry can be broken down into two phases: the photosynthetic carbon fixation occurring in the algae ponds and the extraction and conversion of the biomass carbon into a burnable fuel;
g. the algae oils are extracted by chemical extraction;
h. the algae oil can be refined in a conventional refinery;
i. the hydrogen fuel is distributed by an interstate pipe grid to all coal fired power plants;
j. The biofuels are distributed by the oil industry's infrastructure, gas station and etc.
k. the fuel burned in internal combustion engines, does not have a carbon foot print because, the $CO_2$ is from a displacement process

DESCRIPTION OF THE PREFERRED EMBODIMENTS

In the drawing there is shown a preferred embodiment of the invention wherein either a low rank or high rank coal is partially oxidized in a coal gasification plant and produces hydrogen and a relatively high purity carbon dioxide gas stream. The hydrogen is burned in a modified burner of the coal power generation plant, or any other coal combustion industrial facility. It produces an environmental clean power plant's stack emissions, water vapor. The preferred embodiment captures the carbon dioxide gas at the gasification plant and converts the gaseous $CO_2$ for commercial production into an oil, gasoline, biodiesel fuel, jet fuel, ethanol, or methane gas. The oil conversion is accomplished by a biomass algae process, and grown in an oil plantation's oil paddies.

The coal pile 1 of FIG. 1 is feed by conveyor to the coal gasification plant 2, see FIGS. 3a & 3b. The coal gasification plant 2 converts the coal to hydrogen ($H_2$) gases and concentrates the high purity carbon dioxide. The hydrogen liquid is piped to the electric power generation plant 3 and the electric power plant's burner is modified to burn hydrogen gas and lipid oil. The hydrogen is burned to produce electricity. The stack gas, hydrogen, is environmental benign with 100% water vapor as the stack gas. The carbon dioxide is captured by a bulk gas separation process and piped to the carbon dioxide recovery plant 4. If required, the liquid carbon dioxide is stored in liquid storage tanks 4A, and 4B. The carbon dioxide can be captured in the peak hours and liquefied for storage for use during the daylight hours as an evaporated gaseous carbon dioxide. However, we use artificial sunlight to produce oil during the evening hours, 8760 hours/year.

The gaseous carbon dioxide is injected into the solar powered algae ponds 5 for conversion to oil. The oil plantation's oil paddies converts the carbon dioxide extracted from the coal gasification plant 2; waste gas into biomass, an organic form of carbon which can be stored, converted into a fuel or be burned on-site or off site, or applied to cropland either as a fertilizer or as an inoculant for a self-generating nitrogen and carbon fixing fertilizer.

In terms of fuels, the primary focus here is to convert the biomass formed from the photosynthetic fixation of $CO_2$ into an lipid oil which can be burned in the power plant 3 (FIG. 2 of the advantageous mode of the embodiment, hydrogen/oil fired power plant), or refined for gasoline, biodiesel fuel, or jet fuel.

The system also includes primary harvesting, clarifiers 6, (continuous sedimentation after polyelectrolyte coagulation) to concentrate the cell suspension from 0.025% (w/v) solids to 5%; and a secondary harvesting, centrifuge 7, to further concentrate the slurry to 15% solids. As much of the clarified water as possible is recycled back to the algae pond reactors 5. The water is collected in a water sump 7A and pumped back to a sand type water filter 7B. Nutrients and water makeup 7C are added at the water filter 7B. It is estimated that 95% of the daily harvest volume can be recycled to the algae ponds 5. The limit on this recycled water is determined by the potential to impair growth of the algae as autotoxins accumulate. This results in blow downstream 7D equal to about 20 cubic meters per acre per day. Assuming an average evaporation rate of 0.5 cm per day, the make-up water 7C requirement will be 40 cubic meters per acre per day.

Along with the sunlight, water and carbon, algal growth requires nutrients; nitrogen, phosphorus, sulfurs, and irons 7C. Daily additions of these nutrients are, respectively, 0.1 mt, 0.01 mt, 0.01 mt, and 0.01 mt. If nitrogen fixing algae are cultivated no nitrogen additions are required.

During the summer, approximately 115,000 cfd (1200 gpm over 12 hours) of culture suspension are removed from the pond and put through the harvesting system, Clarifiers 6 & Centrifuge 7. In the winter the ponds will be heated to maintain 100% production capacity. Polymers are added to induce coagulation. Then the stream is clarified using continuous clarifiers 6. The supernatant is returned to the pond via 7A, after the blow down requirement is removed 7D. Sand filtration 7B of the recycle water may sometime be required to remove remaining flocks.

The clarifier 6 slurry, approximately 5% solids (a two hundred fold concentration of solids from the growth ponds), is further thickened using continuous decanting centrifuges 7. The supernatant is combined with the recycled water stream 7A & 7B. The slurry, now 15% solid is ready for processing to liquid fuels by; Chemical Extraction 8, Refinery 9, & Gas Stations 10 or for introduction into the covered lagoon anaerobic digester, Fuel Conversion 11 to be converted into methane and ethanol.

For fuels burned on site (FIG. 2—advantageous mode of the embodiment), whether oil fed back to the coal burning plant, or methane or ethanol burned for electricity generation, steam for MEA reactivation, heating the coke, or steam for gasification the amount of power obtained per ton of $CO_2$ eventually released depends on the ratio of the amount of power generated by the biomass-based fuel to that generated by the original coal powered plant. $CO_2$ Flue Gas or Purge Gas streams are not allowed to escape into the atmosphere. The $CO_2$ is recovered and converted into bio-oil.

After concentration, the biomass is processed according to the desired product, Fuel Conversion 11 or Chemical Extraction 8. Chemical Extraction 8 for liquid fuels, the composition of the biomass can be directed toward carbohydrates for ethanol formation, Fuel Conversion 11, or towards lipids for transesterification to biodiesel fuel or processing to gasoline or jet fuel, Refinery 9. Each of these fuel options has a waste stream of a relatively dilute liquid phase with substantial dissolved organics, and a sludge containing refractory compounds and other unprocessed organic as well as in organics. The latter stream can be thickened and used for fertilizer. The liquid waste stream and the $CO_2$ stream can be recycled back to the growth pond 5.

The equipment for extraction and the conversion of microalgae into Fatty Methyl Esters (FAMES) are, Chemical Extraction 8 & Refinery 9. The conversion of the lipid is a chemical extraction process using butanol 8. One of the most important considerations is to decrease the quantity of water during harvesting, Clarifier 6 & Centrifuge 7. Concentration of algae before harvesting is 0.05%, after harvesting it approaches 15%. Lowering the percent of water decreases, pumping cost, amount of butanol needed for extraction, and the steam energy for evaporation. The boiler most be sized for evaporation, and recovery of the butanol. The waste stream from the extraction contains 69.4% water, 18.5% I-butanol, 9.7% solids, and 2.6% lipid. Additional butanol recovery needs to occur for continuous operation. Additional boiler capacity is not needed, but another evaporative step is required to minimize butanol loss.

The chemical extraction process 8 will produce a 65 to 70% yield of FAMEs from the lipid. The input stream is approximately 97% lipid and 3% non-lipid material. Hexane will be used to recover the FAMEs from the conversion reaction.

The FAMEs are routed to liquid storage in Chemical Extraction 8 for future shipment to a conventional oil refinery 9 to be processed into gasoline, biodiesel fuel, and jet fuel. It is our plan to use the existing infrastructure 10 of the petroleum industry; distribution, marketing, and retail level gas stations. This existing infrastructure will save substantial business development costs, and time.

Further, it is part of this invention that the preferred mode of the embodiment of the combination $CO_2$ Recovery Plant 4 and the $CO_2$ to Oil Plant 5 as depicted in FIG. 2 to produce a hydrogen/oil fuel blend for combustion in the modified burner of the electrical power generation plant 3. This reduces the cost of combustion and increases the coal pile to buss bar efficiency and thereby increasing the overall generation plant's efficiency.

The primary system function of FIG. 2 is as a feedback capacity control to guarantee the production of 600 MWe of electricity. If the 600 MWe output drops, for whatever reason, more lipid oil is allowed to enter the steam boiler to produce 600 MWe of electricity.

It is also part of this invention that any combination of the preferred mode of the embodiment of the oil conversion process as depicted in FIG. 1 and the advantageous mode of the embodiment of the combination hydrogen/oil fuel blend as depicted in FIG. 2 may be used in conjunction with each other for the most efficient energy system for the specific energy needs for the carbon dioxide recovery plant installation.

Although the present invention has been described in conjunction with the preferred embodiments, it is to be understood that modifications and variations may be utilized without departing from the principles and scope of the invention as described by the following claims.

The invention claimed is:

1. A process of capture carbon and storage (CCS Process) by removing the carbon from coal by coking and gasifying solid coke to produce hydrogen gas, Substitute Natural Gas (SNG), Liquid Natural Gas (LNG) and Synfuels of hydrogen and carbon monoxide, the process which comprises:
   a. indirectly heating or baking the coal in an air free atmosphere, wherein lighter constituents are volatilized and heavier hydrocarbons crack thereby liberating hydrogen, methane, carbon dioxide, and carbon monoxide forming a first gas stream, and a residue of a gray hard porous carbon in the form of solid coke;
   b. the gasification of the solid coke of step a by passing high pressure steam with oxygen from an air separation plant through a hot coke bed comprising the solid coke whose temperature is maintained by partial oxidation of the solid coke in the hot coke bed, and thereby producing hydrogen, methane, carbon dioxide, and carbon monoxide gases forming a second gas stream;
   c. combining and conditioning the two gas streams of step a and step b to form a single gas stream and increasing three times the production amount of hydrogen gas from the solid coke of step a;
   d. cooling and removing solid particulate from the hydrogen, carbon monoxide, and methane gases of the single stream in step c;
   e. adjusting the volume ratio of carbon monoxide to hydrogen gases in step d to a 3 to 1 ratio in a shift catalytic reactor with a gas bypass control;
   f. the hydrogen and carbon monoxide gases of the single stream of step d. enter a methanation unit where said gases are converted to high purity methane;
   g. removing the carbon dioxide from the single gas stream in step e by an acid gas separation process;
   h. the hydrogen gas is produced directly by steam reforming of the high purity methane gas of step f over a nickel catalyst into hydrogen and carbon monoxide or synfuel;
   i. the carbon monoxide of step f is shifted to carbon dioxide and removed by a bulk gas separator comprising a Pressure Swing Absorption (PSA), thereby leaving pure 100% hydrogen gas;
   j. the gaseous hydrogen of step h is converted to a liquid with a liquid nitrogen refrigerant from an air separation plant to form cooled compressed hydrogen gas and then pressure reduction of said cooled compressed hydrogen gas is carried out with a Joules-Thompson valve;
   k. the liquid hydrogen of step j is sent by pipeline to an electrical power plant's steam boiler for combustion;
   l. providing algae ponds and allowing sunlight or solar energy, the carbon dioxide from step g and step i, nutrients, and water to react in the algae ponds thereby, causing growth of the algae lipid oil;
   m. the carbon dioxide from step g and step l, is further injected into the ponds with a contactor or absorber tower having an irrigated packed bed of intalox saddles and illuminated with artificial sunlight, for efficient and maximum growth yield of the algae lipid oil;
   n. sending the algae of step l to environmental stress ponds and withholding nutrients, nitrogen and silicon, to increase the production yield of the algae lipid oil;
   o. harvesting the algae from the environmental stress ponds of step n and transferring the algae to clarifiers which act as a product flow accumulator and further serve as the first stage of dewatering;
   p. further dewatering the algae of step o by centrifuging for substantial water removal;
   q. recovered water of step o and step p is drained from the clarifiers and centrifuge sumps to the main water sump and recirculated by pump to a water filtration unit where the water has nutrients, and make-up water is added and blow down water removed;
   r. harvesting crude lipid oil from de-watered algae shells of step p by chemical extraction;
   s. refining the crude lipid oil of step r for conversion into gasoline, biodiesel, jet fuel, methane, and ethanol at oil refineries and the storage of the biofuels;
   t. the crude lipid oil of step r is fed back into a hydrogen fired electric generation power plant as an alternative for combustion in a dual fired fuel burner; and
   u. disposing of spent de-watered algae shells of step r by anaerobic digestion.

2. The process of claim 1, wherein the CCS Process is carried out in a facility remotely located from coal fired power generation plants, and networked together through hydrogen pipe lines to distribute hydrogen fuel as either a liquid or gas.

3. The process of claim 1, wherein the hydrogen fired electric generation power plant of step t requires no bag house, electric precipitators, NOx reduction units, or sulfur scrubbers to produce zero emissions in the stack gas.

4. The process of claim 1, wherein the coal of step a) is dirty coal and the process converts the dirty coal into clean hydrogen.

* * * * *